United States Patent [19]

Takamizawa et al.

[11] Patent Number: 4,539,417
[45] Date of Patent: Sep. 3, 1985

[54] POLY(DIMETHYLSILMETHYLENE) METHYLACETYLENE COMPOUND AND A METHOD FOR THE PREPARATION THEREOF

[75] Inventors: Minoru Takamizawa; Akira Yamamoto; Toshinobu Ishihara; Mistuyoshi Ohshima, all of Niigata, Japan

[73] Assignee: Shin-Etsu Chemical Co., Ltd., Japan

[21] Appl. No.: 658,597

[22] Filed: Oct. 9, 1984

[30] Foreign Application Priority Data

Oct. 11, 1983 [JP] Japan .................................. 58-189540

[51] Int. Cl.$^3$ .............................................. C07F 7/08
[52] U.S. Cl. ................................................... 556/435
[58] Field of Search ........................................ 556/435

[56] References Cited

U.S. PATENT DOCUMENTS 3,178,465 4/1965 Huba et al. ........................ 556/435 X
3,714,118 1/1973 Chandra et al. .................. 556/435 X
4,414,403 11/1983 Schilling et al. ................ 556/435 X Primary Examiner—Paul F. Shaver
Attorney, Agent, or Firm—Toren, McGeady, Stanger, Goldberg & Kiel

[57] ABSTRACT

The invention provides a novel organosilicon compound poly(dimethylsilmethylene) methylacetylene compound of the formula MeC≡C—SiMe$_2$—(CH$_2$—SiMe$_2$)$_n$Me, in which Me is a methyl group and n is a positive integer of 1 to 25. The compound is synthesized by reacting a propynylmagnesium halide of the formula MeC≡CMgX, in which X is a halogen atom, or (propynyl dimethylsilyl)methylmagnesium chloride of the formula MeC≡C—SiMe$_2$—CH$_2$MgCl with chloromethyl dimethyl chlorosilane in the presence of metallic magnesium and hydrolyzing the reaction product. Specifically, 1-propynyl-1,1,3,3,3-pentamethyl disilmethylene, i.e. the inventive compound with n=1, is synthesized by reacting (propynyl dimethylsilyl)methylmagnesium chloride with trimethyl chlorosilane.

5 Claims, 2 Drawing Figures

POLY(DIMETHYLSILMETHYLENE) METHYLACETYLENE COMPOUND AND A METHOD FOR THE PREPARATION THEREOF

BACKGROUND OF THE INVENTION

The present invention relates to a poly(dimethylsilmethylene)methylacetylene compound as a class of novel organosilicon compounds and a method for the preparation thereof.

The present invention has been completed in the course of the inventors' to extensive investigations to discover an organosilicon compound which is useful as a starting material for the preparation of silicon carbide fibers by the pyrolysis of an organosilicon compound.

SUMMARY OF THE INVENTION

The novel organosilicon compound, poly(dimethylsilmethylene)methylacetylene compound, of the invention is a poly(dimethylsilmethylene) having a 1-propynyl group bonded to one of the terminal silicon atoms in a molecule in place of the methyl group and represented, denoting a methyl group by the symbol Me, by the general formula $$MeC{\equiv}C-SiMe_2{-}(CH_2-SiMe_2)_n{-}Me, \quad (I)$$

in which the suffix n is a positive integer from 1 to 25.

The above described novel organosilicon compound can readily be synthesized by the Grignard reaction of chloromethyl dimethyl chlorosilane and a propynyl magnesium halide of the formula MeC≡CMgX, X being a halogen atom, i.e. a Grignard reagent derived from methylacetylene, in the presence of metallic magnesium. Alternatively, the compound can be synthesized by the Grignard reaction of chloromethyl dimethyl chlorosilane and (dimethylpropynylsilyl)methyl magnesium chloride of the formula $$MeC{\equiv}CSiMe_2.CH_2MgCl, \quad (II)$$

i.e. a Grignard reagent derived from chloromethyl propynyl dimethyl silane of the formula $$MeC{\equiv}CSiMe_2.CH_2Cl \quad (III)$$

in the presence of metallic magnesium.

When the inventive compound of which the suffix n in the formula (I) is 1, i.e. 1-propynyl-1,1,3,3,3-pentamethyldisilmethylene, is desired, in particular, the Gringard reaction should be performed between trimethyl chlorosilane and the Grignard reagent expressed by the formula (II) above.

DETAILED DESCRIPTION OF THE PREFERRED EMBODIMENTS

Figure 1:
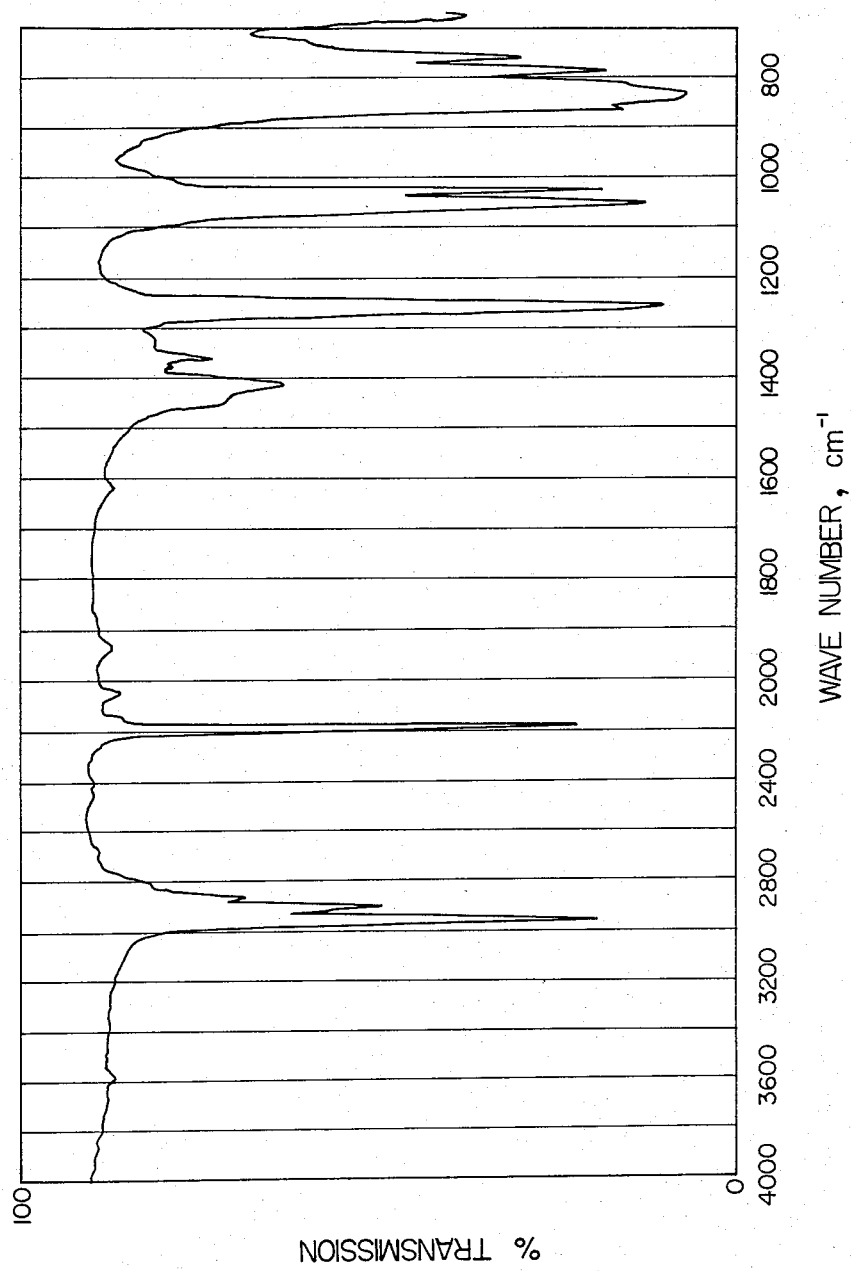
FIGS. 1 and 2 are each in infrared absorption spectrum of the inventive compound prepared in Example 1 or Example 2, respectively.

The novel organosilicon compound of the invention represented by the general formula (I) above is characteristic with the propynyl group MeC≡C— bonded to one of the terminal silicon atoms in the poly(dimethylsilmethylene) compound and the compound is useful, by virtue of the reactive propynyl group in the molecule, as a stabilizing agent of various halogenated compounds. The compound is also useful as a lubricant.

Further, the triple bond in the propynyl group is capable of pertaining to polymerization or crosslinking of the compound and the thus polymerized or crosslinked product having an increased molecular weight is particularly useful as a starting material for the preparation of silicon carbide fibers or powdery silicon carbide usable as a filler.

As is described above, the poly(dimethylsilmethylene)methylacetylene of the invention can be synthesized by the Grignard reaction between chloromethyl dimethyl chlorosilane and a propynylmagnesium halide taking place in a solvent such as tetrahydrofuran under reflux followed by the hydrolysis of the condensation product according to the following reaction scheme:

$$MeC{\equiv}CMgX + ClSiMe_2.CH_2Cl + MG \rightarrow MeC{\equiv}C-SiMe_2CH_2MgCl$$

$$MeC{\equiv}CSiMe_2CH_2MgCl + ClCH_2SiMe_2Cl + Mg \rightarrow MeC{\equiv}CSiMe_2.CH_2SiMe_2.CH_2MgCl$$

$$MeC{\equiv}CSiMe_2.CH_2SiMe_2.CH_2MgCl + H_2O \rightarrow MeC{\equiv}CSiMe_2.CH_2SiMe_3 + MgCl(OH)$$

That is, the propynylmagnesium halide is first prepared in tetrahydrofuran as the solvent and metallic magnesium is added to the thus obtained solution of the Grignard reagent followed by dropwise addition of chloromethyl dimethyl chlorosilane to effect the Grignard reaction. The reaction mixture is then subjected to hydrolysis by use of a saturated aqueous solution of ammonium chloride and the organic solution taken by separating from the reaction mixture is distilled to remove the organic solvent so that the desired product can be obtained. The molecular weight or the suffix n in the formula (I) can be controlled by adequately selecting the molar ratios of the chloromethyl dimethyl chlorosilane and metallic magnesium to the Grignard reagent. When the ratios are increased, the resultant poly(dimethylsilmethylene)methylacetylene compound has an increased molecular weight or vice versa. At any rate, it is difficult to prepare the compound of the formula (I) in which the suffix n has a value larger than 25. Usually, the reaction product obtained in the above described manner is a mixture of several molecular species of the formula (I) having different values of the suffix n and the individual molecular species can be fractionated into the respective isolated pure forms by the chromatographic techniques.

Alternatively to the above described synthetic procedure, the poly(dimethylsilmethylene)methylacetylene of the invention can be synthesized via chloromethyl propynyl dimethylsilane of the formula (III). Thus, a propynylmagnesium halide and an equimolar amount of chloromethyl dimethyl chlorosilane are reacted in the absence of metallic magnesium to form the compound of the formula (III) which is then converted to the corresponding Grignard reagent of the formula (II) and this compound is further reacted with chloromethyl dimethyl chlorosilane in the presence of metallic magnesium in a solvent such as tetrahydrofuran under reflux. The procedure is expressed by the following reaction scheme:

$$MeC{\equiv}CMgX + ClSiMe_2.CH_2Cl \rightarrow MeC{\equiv}C-SiMe_2.CH_2Cl; \text{ and}$$

$$MeC{\equiv}C.SiMe_2.CH_2Cl + nClSiMe_2.CH_2Cl + nMg \rightarrow MeC{\equiv}C-SiMe_2-CH_2{-}(SiMe_2)_n{-}Me.$$

When the desired compound is 1-propynyl-1,1,3,3,3-pentamethyldisilmethylene which is the compound of the general formula (I) of which the suffix n is equal to 1, in particular, this compound can be readily synthesized, in addition to the above described synthetic methods, by the reaction of a propynyldimethylsilylmethyl magnesium halide of the formula (II) with trimethyl chlorosilane in a solvent such as tetrahydrofuran at a relatively low temperature of, for example, about 30° C. according to the following reaction scheme:

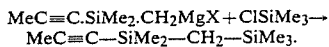

MeC≡C.SiMe₂.CH₂MgX + ClSiMe₃ →
MeC≡C—SiMe₂—CH₂—SiMe₃.

In the following, the synthetic method of the inventive compounds and the results of identification of the product compounds are described in more detail by way of examples.

EXAMPLE 1

Into a flask of 500 ml capacity were introduced 12 g (0.5 mole) of metallic magnesium and 250 ml of tetrahydrofuran and then 51 g (0.5 mole) of ethyl bromide were added dropwise into the mixture kept at 30° C. in the flask under a stream of nitrogen gas to form ethylmagnesium bromide. Into the reaction mixture kept at 40° to 50° C. was blown 0.5 mole of methylacetylene over a period of 1 hour to form 1-propynylmagnesium bromide. Thereafter, 57.2 g (0.4 mole) of chloromethyl dimethyl chlorosilane were added dropwise into this reaction mixture kept at 30° C. followed by aging at 50° C. for 1 hour. The reaction mixture was subjected to hydrolysis with a saturated aqueous solution of ammonium chloride and the organic solution taken by phase separation from the mixture was distilled to give 47 g (0.32 mole) of chloromethyl propynyl dimethyl silane boiling at 154° C.

Separately, 7.2 g of metallic magnesium and 200 ml of tetrahydrofuran were introduced into another flask of 500 ml capacity and 47 g of the above obtained chloromethyl propynyl dimethyl silane were added dropwise into the reaction mixture under reflux in the flask over a period of 1 hour to form the Grignard reagent of (propynyldimethylsilyl)methylmagnesium chloride. Thereafter, 33 g (0.3 mole) of trimethyl chlorosilane were added dropwise into the reaction mixture kept at 30° C. in the flask to be reacted with the Grignard reagent followed by aging at 50° C. for 1 hour. The reaction mixture was subjected to hydrolysis with a saturated aqueous solution of ammonium chloride and the organic solution taken by phase separation from the mixture was distilled to give 47 g of a fraction boiling at 173° C. The purity of this fraction obtained by the distillation was 99% by weight as determined by the gas chromatography.

The above obtained fraction was analyzed by the gas chromatographic-mass spectrometer (GC-MS) to identify the compound as the principal ingredient thereof. Thus, three strong peaks were found at m/e=169, 97 and 73. By analogy with the mass spectra of several silane compounds, it was presumable that the peak at m/e=169 was assignable to the fragment ions formed from the molecules of the compound per se with a methyl group removed from each molecule so that the molecular weight of the compound would be 184 in a fair assumption. Further, the peaks at m/e=73 and 97 were respectively assignable to the fragment ions of trimethylsilyl groups and propynyldimethylsilyl groups.

The infrared absorption spectrum of this fraction was as shown in FIG. 1 in which the absorption bands at 2195 cm⁻¹ and 2960 cm⁻¹ could be assigned to the carbon-to-carbon triple bond and the silicon-to-methyl linkage, respectively.

Further, the NMR absorption spectrum of the compound was measured in a carbon tetrachloride solution with tetramethylsilane as the internal reference to find the absorption maxima at 1.74 ppm for the protons in C≡C—CH₃, at −0.21 ppm for the protons in Si—CH₂—Si and at 0.11 ppm and 0.05 ppm for the protons in Si—CH₃. The intensity ratio of these absorptions was 3:2:15 as determined on the integral curves corresponding thereto.

The above given analytical results as well as the synthetic procedure supported that this compound was 1-propynyl-1,1,3,3,3-pentamethyl disilmethylne of the formula

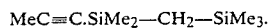

MeC≡C.SiMe₂—CH₂—SiMe₃.

EXAMPLE 2

Ethylmagnesium bromide was prepared in a similar manner to Example 1 from 12 g (0.5 mole) of metallic magnesium in 250 ml of tetrahydrofuran and 5.4 g (0.05 mole) of ethyl bromide instead of 54 g (0.5 mole). Then, 10 ml of a tetrahydrofuran solution containing 2 g (0.05 mole) of methylacetylene were added dropwise to the reaction mixture kept at 40° to 50° C. to form 1-propynylmagnesium bromide. Further, 57.2 g (0.4 mole) of chloromethyl dimethyl chlorosilane were added dropwise into the reaction mixture kept at 50° to 70° C. over a period of 4 hours followed by aging at 66° C. for 2 hours. The reaction mixture was subjected to hydrolysis with a saturated aqueous solution of ammonium chloride and the organic solution taken from the mixture by phase separation was distilled under reduced pressure to remove the solvent leaving 31 g of a viscous liquid residue as the reaction product.

Figure 2:
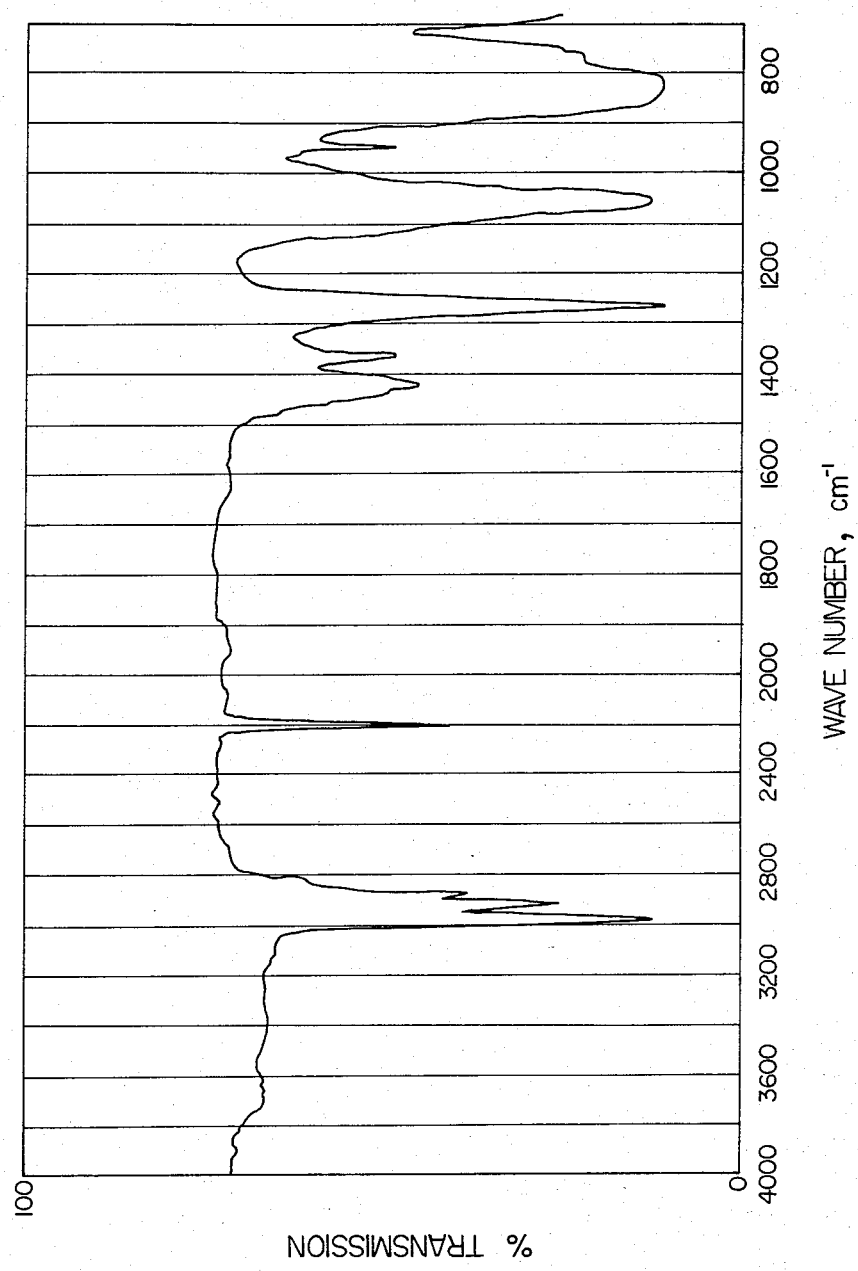

The infrared absorption spectrum of this reaction product was as shown in FIG. 2 in which the absorption bands appearing at 2195 cm⁻¹ and 2960 cm⁻¹ could be assigned to the carbon-to-carbon triple bond and to the silicon-to-methyl linkage, respectively.

The product was subjected to the GC-MS analysis to give, in addition to the principal peak at m/e=169, strong peaks at m/e=241, 73 and elsewhere. The principal peak at m/e=169 was assignable, as in Example 1, to the fragment ions derived from the molecules of 1-propynyl-1,1,3,3,3-pentamethyl disilmethylene with a methyl group removed from each molecule. The peak at m/e=241 could be assigned, by analogy with the peak at m/e=169, to the fragment ions formed from molecules having a molecular weight of 256 with a methyl group removed from each molecule. This compound of molecular weight 256 was presumably 1-propynyl-1,1,3,3,5,5,5-heptamethyl trisilmethylene of the formula MeC≡C—SiMe₂—CH₂—SiMe₂CH₂—SiMe₃, i.e. the compound of the general formula (I) in which the suffix n was equal to 2.

The reaction product was further analyzed by the gel permeation chromatography (GPC) to give a main fraction corresponding to 1-propynyl-1,1,3,3,3-pentamethyl disilmethylene and 10 additional fractions containing molecular species of higher molecular weights than the above mentioned compound. Each of these fractions for the species of higher molecular weights was found to correspond to one of the compounds of the general formula (I) in which the suffix n had a value of 1 to 10 in this order by the comparison with the calibration curves. The subsequent eluate from the GPC containing the molecular species of still higher molecular weights could not be separated into fractions each containing a single species although it was found that the amount of the polysilmethylene compounds decreased as the molecular weight or degree of polymerization increased.

The NMR absorption spectrum of the reaction product was measured in the same manner as in Example 1 to give absorptions at 1.74 ppm for the protons in C≡C—CH$_3$, at −0.21 ppm for the protons in Si—CH$_2$—Si and at 0.11 ppm and 0.05 ppm for the protons in Si—CH$_3$, of which the absorption at 0.11 ppm was ascribable to the protons in —Si(CH$_3$)$_2$— and the absorption at 0.05 ppm was ascribable to the protoons in —Si(CH$_3$)$_3$. Estimation was made from the ratio of the integrated intensities of these two absorptions that the average number of the suffix n in the general formula (I) for the reaction product as a mixture of several species with different molecular weights was about 8.7.

What is claimed is:

1. A poly(dimethylsilmethylene)methylacetylene compound represented by the general formula

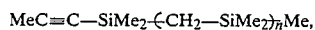

in which Me is a methyl group and n is a positive integer of 1 to 25.

2. The poly(dimethylsilmethylene)methylacetylene compound as claimed in claim 1 wherein the positive integer n is 1.

3. A method for the preparation of a poly(dimethylsilmethylene)methylacetylene compound represented by the general formula

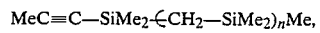

in which Me is a methyl group and n is a positive integer of 1 to 25, which comprises reacting a propynylmagnesium halide of the formula MeC≡CMgX, in which Me is a methyl group and X is a halogen atom, with chloromethyl dimethyl chlorosilane in the presence of metallic magnesium and hydrolyzing the reaction product.

4. A method for the preparation of a poly(dimethylsilmethylene)methylacetylene compound represented by the general formula

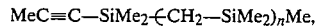

in which Me is a methyl group and n is a positive integer of 1 to 25, which comprises reacting (propynyl dimethylsilyl)methylmagnesium chloride of the formula

in which Me has the same meaning as defined above, in the presence of metallic magnesium and hydrolyzing the reaction product.

5. A method for the preparation of 1-propynyl-1,1,3,3,3-pentamethyl disilmethylene of the formula

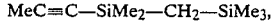

in which Me is a methyl group, which comprises reacting (propynyl dimethylsilyl)methylmagnesium chloride of the formula

in which Me has the same meaning as defined above, with trimethyl chlorosilane.

* * * * *